United States Patent [19]

Kashima

[11] Plant 4,137

[45] Oct. 25, 1977

[54] CHRYSANTHEMUM NAMED IMPERIAL YELLOW

[76] Inventor: Takaaki Peter Kashima, 923 Woodside Road, Redwood City, Calif. 94061

[21] Appl. No.: 758,339

[22] Filed: Jan. 10, 1977

[51] Int. Cl.[2] ..... A01H 5/00

[52] U.S. Cl. ..... Plt./78

[58] Field of Search ..... Plt./77-78

*Primary Examiner*—Robert E. Bagwill

*Attorney, Agent, or Firm*—Rummler and Snow

[57] ABSTRACT

A new variety of chrysanthemum plant originated as a sport of the cultivar No. 2 Yellow Albatross and distinguished from its parent by its lighter flower color, larger flower size and more incurved flower form, longer form retention, and increased stem diameter and length.

1 Drawing Figure

BACKGROUND OF THE NEW PLANT

This new chrysanthemum variety was discovered by me at Redwood City, Calif., in 1973 among a group of No. 2 Yellow Albatross chrysanthemum plants (unpatented) grown by me for commercial production of cut flowers and potted plants, the new plant being found as a sport of one of the Yellow Albatross plants in the said group. Because of its much larger flower size and lighter color, this sport was asexually reproduced by me for propagation through several generations to determine its growing characteristics and commercial value. This propagation was carried on by me and under my direction at Redwood City, Calif., by means of cuttings and the plants were observed to have many distinctive and valuable improvements over the parent variety which hold true from generation to generation and appear to be firmly fixed. Propagation of this new plant by means of vegetative cuttings is now being done at Redwood City, Calif., for the commercial market.

DESCRIPTION OF THE DRAWINGS

My new variety of chrysanthemum is illustrated by the accompanying drawings in which, on sheet 1, the left hand view shows the flower in full bloom and the right hand view shows a comparison of the flower on the new plant with a typical flower of the parent variety which is positioned at the left in that view; and sheet 2 shows pen-and-ink tracings of typical leaves of the new plant variety taken from a single stem. The flower views are in full color as nearly true as it is reasonably possible to obtain by conventional photographic procedures and considering the very light shades of yellow involved.

DESCRIPTION OF THE NEW PLANT

The following is a detailed description of my new chrysanthemum plant with color designations according to The R.H.S. Colour Chart published by The Royal Horticultural Society at London, England.

THE PLANT

Origin: Sport.
Parentage: No. 2 Yellow Albatross (unpatented).
Classification:
*Botanic.*—*Chrysanthemum morifolium.*
*Commercial.*—Standard, incurved.
Form: Perennial herbaceous bush.
Height: 2 to 4 feet.

Growth: Terminal. Average growth, upright and sturdy with very good strength.
Branching: Normal under natural conditions.
Foliage: 5 to 7 leaves on about 6 inches of stem.
*Size of leaf.*—Length — $4\frac{7}{8}$ to 6 inches. Width — $2\frac{5}{8}$ to $3\frac{5}{8}$ inches.
*Shape.*—Lobed, lanceolate, and slightly serrated.
*Surface texture.*—Canescent.
*Color.*—Upper side — 137A. Under side — 146A.
*Venation.*—Pinnately.
*Petioles.*—$\frac{7}{8}$ to 1 inch long.

THE BUD

Form: Semisphere.
Size: Large.
*Diameter.*—$\frac{5}{8}$ to $\frac{7}{8}$ inch; Depth — 5/16 to 7/16 inch.
Opening rate: Slow.
Color:
*When phyllaries first divide.*—1C.
*When florets begin to unfurl.*—10A.
Phyllaries: Pubescent and spear shaped.
*Color.*—Inside — 144A. Outside — 147B.
Peduncle: Length — $1\frac{1}{2}$ to $2\frac{7}{8}$ inches.
*Strength.*—Erect and strong.
*Surface aspect.*—Pubescent.

THE FLOWER

Response: 9 week.
Recommended flowering: Oct. 23 to Nov. 1.
Blooms: Flower type — Incurved.
*Borne.*—A head of many florets borne on a receptacle.
*Shape.*—Flat at first, becoming more globular as bloom matures.
*Size.*—Very large, 5 to $7\frac{1}{2}$ inches in diameter; $3\frac{1}{2}$ to 4 inches in depth.
*Florets.*—Number 450 to 500. Form: Lanceolate with acute apex. Color: Outer florets: Upper side—2D, 3D, 4C; Reverse side—4D. Inside florets: Upper side—5B, 5C, 6B, 6C; Reverse side—5D, 6D. Firmness: Medium. Appearance: Shiny. Discoloration: Slight fade after full bloom.
*Peduncle.*—$1\frac{1}{2}$ to 4 inches long, upright and sturdy. Color: 147B.
*Fragrance.*—Typical chrysanthemum.
*Persistence.*—Florets hang on and dry.
*Effect of weather.*—Recommended for greenhouse culture only.
*Lasting quality.*—On plant — 3 weeks. As cut flower — 12 to 16 days.

REPRODUCTIVE ORGANS

Stamens: Synoecious, connate by their anthers, to form a cylinder about the style.

*Anthers.*—Length — 1/16 inch. Color — Yellow.

*Filaments.*—Length — 3/16 inch.

Pistils: Number — One to each ray floret.

*Length.*—7/32 to 9/32 inch.

*Stigmas.*—Color — Yellow.

Ovaries: Inferior bicarpellate.

This new chrysanthemum plant most nearly resembles its parent No. 2 Yellow Albatross differing mainly by its larger flower size and lighter coloration, as well as by its larger foliage and greater stem size and length. A more detailed comparison of the new plant and its parent is shown by the following table.

I claim:

1. A new and distinct variety of chrysanthemum plant, substantially as herein shown and described, characterized by the large size of its blooms and their light yellow coloration, the greater plant height and the increased size, strength and length of its stems.

| | Imperial Yellow | No. 2 Yellow Albatross |
|---|---|---|
| Bloom: | | |
| Size: | 5 - 7 ½ inches | 4 - 5 inches |
| Form: | Incurved - more incurved than No. 2 Yel. Albatross. | Incurved - less incurved than Imperial Yellow. |
| Form Retention: | Minimal reflexing under high temperatures. | Considerable reflexing under high temperatures. |
| Color: | | |
| Outer Petals - | | |
| Upper Side | 2D, 3D, 4C | 3C, 3D, 4C |
| Reverse Side | 4D | 4D |
| Inner Petals - | | |
| Upper Side | 5B, 5C, 6B, 6C | 5B, 6B, 6C |
| Reverse Side | 5D, 6D | 5D, 6D |
| Petals: | | |
| Length | 2⅝ - 3¼ inches | 2⅜ - 2⅝ inches |
| Width | ¾ - ⅞ inches | ⅝ - ¾ inches |
| Texture | Smooth | Smooth |
| Foliage: | | |
| Quantity | 5-7 leaves on 6 inch stem. | Same |
| Size: | | |
| Length | 4⅞ - 6 inches | 4¼ - 5 inches |
| Width | 2⅝ - 3⅝ inches | 2¼ - 2½ inches |
| Texture: | Very coarse | Coarse |
| Shape: | Lobed, lanceolate | Same |
| Plant: | | |
| Height: | 2 - 4 feet | 5 - 9% shorter than Imperial Yellow. |
| Stem Diameter: | 5/16 - 7/16 inches | ¼ - ⅜ inch |

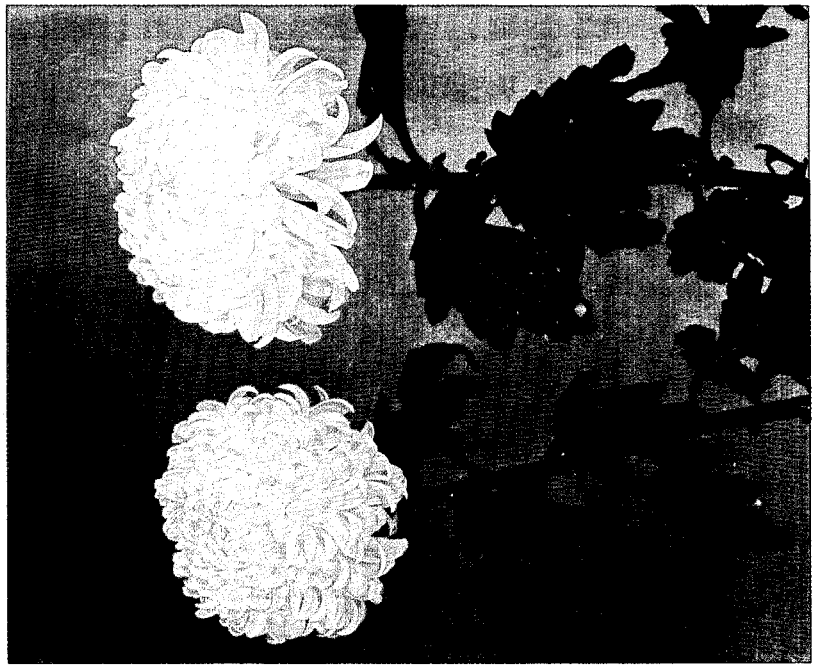
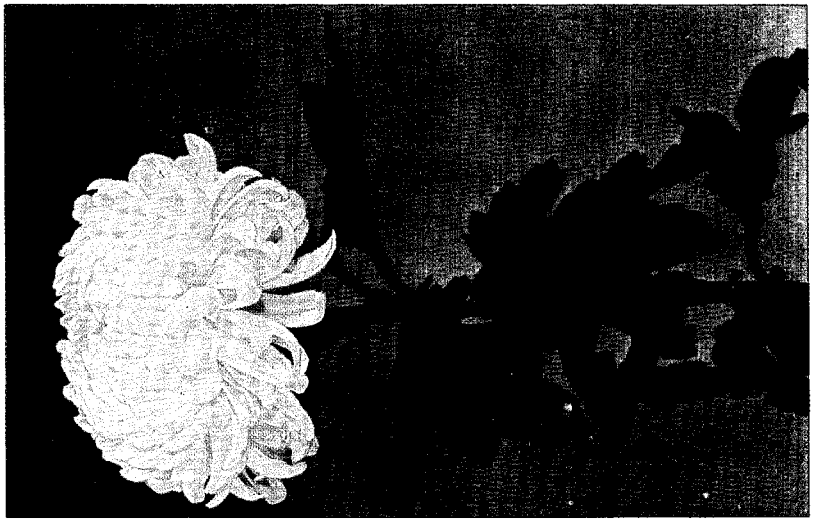

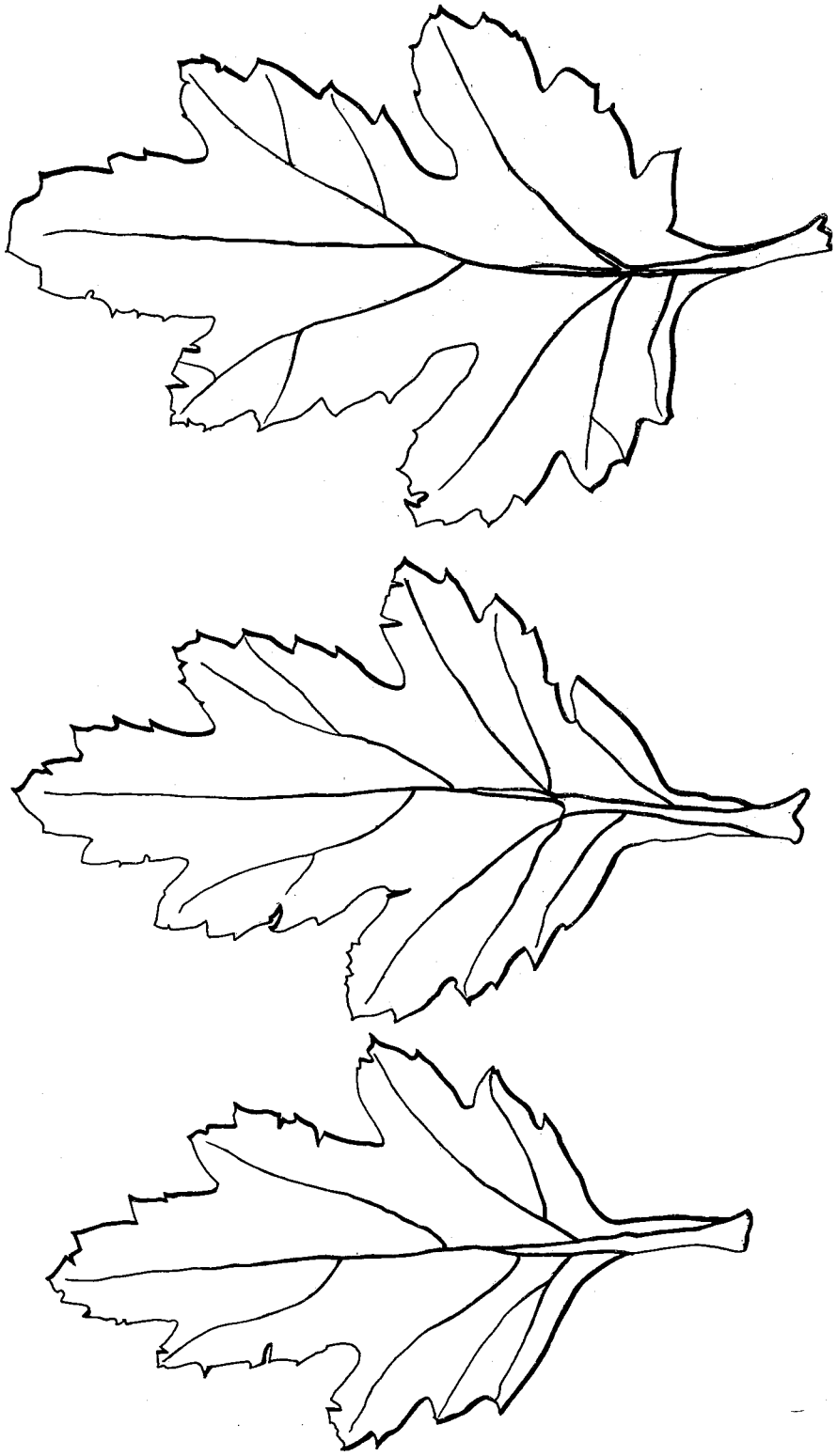

* * * * *